(12) United States Patent
Aben et al.

(10) Patent No.: US 7,155,046 B2
(45) Date of Patent: Dec. 26, 2006

(54) METHOD OF DETERMINING PHYSICAL PARAMETERS OF BODILY STRUCTURES

(75) Inventors: Jean-Paul Maria Michel Aben, Limbricht (NL); Coenraad Christiaan Albert Lokkerbol, Maastricht (NL)

(73) Assignee: Pie Medical Imaging BV, Maastricht (NL)

( * ) Notice: Subject to any disclaimer, the term of this patent is extended or adjusted under 35 U.S.C. 154(b) by 708 days.

(21) Appl. No.: 10/365,016

(22) Filed: Feb. 12, 2003

(65) Prior Publication Data

US 2004/0161137 A1 Aug. 19, 2004

(51) Int. Cl.
*G06K 9/00* (2006.01)

(52) U.S. Cl. .................. 382/130; 600/372; 424/9.4

(58) Field of Classification Search ............... 382/128, 382/129, 130, 131, 132–134, 154; 128/916, 128/922, 130; 600/407–409, 443, 447, 449, 600/461, 437, 509, 372; 606/130, 426, 429
See application file for complete search history.

(56) References Cited

U.S. PATENT DOCUMENTS

| 5,261,404 | A | * | 11/1993 | Mick et al. | 600/425 |
| 5,389,101 | A | * | 2/1995 | Heilbrun et al. | 606/130 |
| 5,531,520 | A | * | 7/1996 | Grimson et al. | 382/131 |
| 5,690,118 | A | * | 11/1997 | Sornmo et al. | 600/509 |
| 6,228,028 | B1 | * | 5/2001 | Klein et al. | 600/437 |
| 6,585,651 | B1 | * | 7/2003 | Nolte et al. | 600/449 |

OTHER PUBLICATIONS

Longuet-Higgins, H.C.; *A Computer Algorithm for Reconstructing a Scene from two Projections; Nature*, v. 293: 133-135; Sep. 10, 1981.
MacKay, S. et al., *Graphics Methods for Tracking Three-Dimensional Heart Wall Motion*; Computers and Biomed. Res. 15:455-473, Jan. 29, 1982.
Fencil, L.E. et al.; *Accurate Analysis of Blood Vessel Sizes and Stenotic Lesions using stereoscopic DSA System*; Investigative Radiology; 23:33-41; Jan. 1988.
Gronenschild, E.; *CAAS II: A Second Generation System for Off-Line and On-Line Quantitative Corporary Angiography*; Cath. and Cardio. Diag. 33:61-75 (1994).
Gronenschild, E.; *Correction for Geometric Image Distortion in the X-Ray Imaging Chain; Local Technique Versus Global Technique*; Med. Phys. 26:Dec. 12, 1999.

* cited by examiner

*Primary Examiner*—Jingge Wu
*Assistant Examiner*—Abolfazl Tabatabai
(74) *Attorney, Agent, or Firm*—Woodard, Emhardt, Moriarty, McNett & Henry LLP (57) ABSTRACT

A method is disclosed to accurately determine spatial parameters (for example, the diameter, cross-sectional area and segment length) of bodily structures like human arteries. This is done by determining the three-dimensional position of these structures from two monoplane X-ray angiographic images obtained at arbitrary but different orientations with respect to the structure of interest. The images may be taken at a different moment, so a monoplane X-ray system can be used. Movement of the structure of interest in between the two X-ray exposures is allowed. The three-dimensional information obtained this way is subsequently used to correct the measurements of above mentioned parameters for commonly encountered error sources.

12 Claims, 5 Drawing Sheets

METHOD OF DETERMINING PHYSICAL PARAMETERS OF BODILY STRUCTURES

BACKGROUND

The present invention relates generally to image analysis, and more particularly to the analysis of images of bodily structures, where those images are used for spatial measurements of those structures.

The main arteries, like the aorta, the coronary arteries, the carotid arteries, the renal arteries and the femoral arteries provide the body with blood. Artery stenosis is an abnormal condition characterized by the constriction or narrowing of these vital arteries by a substance known as plaque, that prevents proper circulation of the blood. Plaque is a localized area of arteriosclerosis. Arteriosclerosis is a pathological condition that deposits lipids (fatty substances) and a proliferation of fibrous connective tissue on the inner walls of the arteries. Also anatomical (inherited) restrictions of the arteries exist (for instance because of tortuous vessels) or enlargements of the arteries (aneurysms) that strongly influence the flow of blood or, as in the latter case, could even endanger the life of the patient by spontaneous rupture of the artery concerned.

Standard treatments for these pathological conditions consist of opening up the stenosed arteries by the use of drugs, or when this proves ineffective, by mechanical means. For example, one may force the opening of the artery by inflation of a little balloon inside the stenosed area ("dotter" or "PTA" procedure) often followed by the placement of a metallic frame ("stent") inside the artery to prevent it from re-occlusion. Stent-like structures can also be used to treat the dangerous local enlargements of arteries. Important for these treatments is to know the exact position, shape, and extent of the stenoses or aneurysms. This will strongly influence the choice of treatment.

An angiography-based diagnosis is the current standard for determining the extend of stenosis. Angiography is a special X-ray procedure that takes pictures ("angiograms") of blood vessels. This diagnostic technique makes use of a radiopaque contrast medium, which is a chemical substance that strongly absorbs passing X-rays. Angiography is the X-ray visualization of the internal anatomy of the heart and/or blood vessels after the introduction of a radiopaque contrast medium into the blood. The contrast medium may be injected into an artery or a vein or introduced in a peripheral artery through a catheter (hollow tube) inserted in the artery. The radiologist carefully threads it into the blood vessel and guides it to the area to be studied, under continuous X-ray vision. When the catheter reaches the site under investigation, X-ray contrast medium is injected through the catheter and makes the artery with all its irregularities and blockages clearly visible.

The term "angiogram" refers to the radiographic image of a blood vessel produced by angiography. Angiograms have darkened areas that represent open channels in blood vessels caused by the contrast medium blocking the X-rays. Digitizing the resulting images makes it possible to apply image processing techniques to the images. One of these techniques is to perform semi-automatic quantitative measurements of the vascular system such as vessel segment length, diameter, cross-sectional area, and the amount of narrowing of a vessel.

Nowadays most examinations of vessel morphology are done using angiographic images acquired with a monoplane X-ray system. The term monoplane refers to the fact that such a system can only acquire an X-ray image from one direction at a time. In contrast, biplane X-ray systems can acquire images from two directions simultaneously.

Performing quantitative measurements based upon a monoplane angiographic image has two important shortfalls that arise from the near absence of information about the three-dimensional position of the vascular structure. The image is in fact a projection that projects all three dimensional structures onto a two-dimensional plane. The two shortfalls are out-of-plane calibration errors and "foreshortening," each of which will now be described.

When using a monoplane X-ray image, one must "calibrate" the image in order to make absolute measurements. That is, the relationship between pixel size and real-world size needs to be determined. This can be done by including an object of known size in the recorded image. Problems arise when the object used for calibration is not in the same plane (parallel to the input screen of the image intensifier) as the structure under investigation. This will result in the calibration object being magnified differently than the structure, and hence in an incorrect measurement. In other words, every part of the vessel that is located in a different plane than the calibration object is magnified differently. This error source is called "out-of-plane calibration."

Generally, because of its intrinsic shape, the structure under investigation typically will not lie exactly in the image plane. If a structure, e.g., a vessel, has a directional component normal to the image plane, the length of a segment of that vessel, when projected on the image plane, will not equal its real three-dimensional length. This phenomenon, leading to errors in length measurements, is called "foreshortening."

To overcome these problems one needs a more accurate, three-dimensional (3-D) representation of the position and shape of the structure under investigation.

Several methods have been developed that derive three-dimensional information from two digital, two-dimensional images. Stereoscopic digital angiography has been used in the calculation of three-dimensional position and orientation information of vessels (L. E. Fencil et al., Investigative Radiology, December 1987). However, stereoscopic determination of three-dimensional vessel position becomes less accurate if the main direction of the vessel is perpendicular to the direction of the stereoscopic shift. Thus, the reliability of this method in determining three-dimensional vessel structure depends on the orientation of the vessels themselves. This is clearly undesirable.

In U.S. Pat. No. 4,630,203, Szirtes describes a technique for the three-dimensional localization of linear contours appearing in two stereoscopic images. However, this method also suffers from the limitation that the contour must not lie in the direction of the stereoscopic shift. In addition, a separate calibration step is required in this method to determine the three-dimensional locations of the X-ray sources relative to the imaging plane.

Several workers have developed methods to derive three-dimensional structure from two radiographic images that are obtained in exactly orthogonal directions. The prerequisite that the images must be obtained in exactly orthogonal directions is a clear drawback of this method. This may be difficult to achieve in practice. In addition, determination of the positions of vessel segments perpendicular to one of the imaging planes is difficult or impossible with these methods.

To address these problems, a method has been developed that allows calculation of three-dimensional vascular structure from two images obtained at arbitrary orientations (see S. A. MacKay et al., Computers and Biomedical Research, Vol. 15, p. 455, 1982). This method requires a calibration step on an object of known dimensions in the same X-ray system configuration as is used to image the patient. This calibration can be done before or after imaging the patient. This method is also referred to as the "calibrated epipolar geometry" method.

In U.S. Pat. No. 4,875,165, Fencil et al. describe a method that requires a pair of biplane images as input and no calibration step, based upon the theoretical work of H. C. Longuet-Higgins, Nature, Vol. 293, p. 133, 1981. K. R. Hoffmann, U.S. Pat. No. 5,859,922, describes a method using several biplane images with the use of a calibration object. Both methods, however, have the drawback that a biplane X-ray system (that is, an X-ray system capable of making two recordings from different orientations simultaneously) is needed.

Some other methods are aimed at reconstruction of the complete 3-D vascular tree from two or more images, but often require biplane X-ray systems. See for instance U.S. Pat. No. 6,047,080 to Chen et al. and U.S. Pat. No. 6,169,917 to Masotti et al.

SUMMARY

Various embodiments of the present invention address problems encountered with some other parameter determination systems. For example, with many prior multi-image systems, no movement of the patient table is allowed between the collection of the two images. However, if a radiologist performing an angiographic examination has to reposition the patient table height or horizontal position between recording of the images in order to get the vessel under investigation in optimal view, measurements using other techniques can be adversely affected. The present method, therefore, allows such movements without compromising the accuracy of the results. Further, in some embodiments of the present invention, the calibration step can be done simultaneously with the acquisition of the image containing the vessel.

A method according to one embodiment of the present invention allows two independently acquired monoplane angiographic images as input for calculation of the three-dimensional midline position of the three-dimensional vascular structures. This means that the two images can be obtained using a monoplane X-ray system (though a biplane system may also be used) at arbitrary orientations. Furthermore, the images may also be obtained with an intervening movement of the patient table.

DESCRIPTION

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

Generally, the image capture and analysis system and method illustrated in FIGS. 1–5 provides for the capture of two digital images, each of a reference object and a bodily structure, such as an artery to be stenosed. In the example presented, the two images are processed to determine the size, shape, and position of the structure.

An example arrangement for capturing images for use in one embodiment of the present invention will now be discussed with reference to FIG. 1. System 100 includes a C-arm 110 that supports X-ray tube 120 and image intensifier 130. Patient table 140 supports the patient whose vessel 160 is under investigation in this example. Calibration object 150 is placed so that it appears in the captured images, and will be discussed in further detail below. A normal cath-lab imaging procedure can be followed, as will be understood by those skilled in the art, with the exceptions discussed in the following paragraph, to assure that the required input for the three-dimensional reconstruction is available.

First, calibration object 150 is placed in the imaging scene. For example, calibration object 150 may be placed beneath the patient, on or under patient table 140, in a pocket of the patient's gown, or other location. Then two images are taken of the vessel that is being investigated. The spatial angle between the two normal vectors for the imaging is greater than −180° and less than 180° and not equal to 0°. Preferably the spatial angle is at least 30°. THE angulation angle γ, rotation angle θ, and source-to-intensifier distance SID should be known. Again, the vessel 160 under investigation and at least a portion of calibration object 150 must both be visible in both images. Between the recording of the two images, the customary patient table movement is allowed. The only requisite is that the vessel position relative to the calibration object does not change. In some embodiments, additional images may be captured, then a pair of images be selected for further analysis.

Before the three-dimensional reconstruction can be used in practice, a few parameters should be determined. In most embodiments, this only needs to be done once and will in general take place at the installation of the software and hardware. In this example, the following parameters will be determined at installation: geometric image distortion, pixel size at the surface of the image intensifier, and systematic error in the X-ray system geometry.

The geometric image distortion will be determined for a number of different orientations of C-arm 110. Geometric image distortion is a distortion resulting from imperfect imaging by the X-ray imaging chain (image intensifier, video camera digitizer) and may be a non-negligible contribution to image errors. One typical distortion factor inherent to the use of image intensifiers is the so-called "pincushion" distortion. Geometric distortion is also dependent on the orientation of the X-ray system with respect to the earth because of the influence of the earth's magnetic field and gravity. In this embodiment, therefore, the geometric distortion is determined for different orientations of C-arm 110 by making a recording of an image grid of known dimensions (not shown, but well known in the art). Correction parameters are automatically derived, as is within the ability of those skilled in the art. See, for example, Gronenschild, E., J. Janssen, et al. "The accuracy and reproducibility of a global method to correct for geometric image distortion in the x-ray imaging chain." Med. Phys. 24(12), pp. 1875–88 (1997).

The pixel size at the surface of the image intensifier will be determined, as is within the ability of those skilled in the art.

The systematic error in the X-ray system geometry as reported by this system needs to be determined to make correction possible.

Validation Data

To determine the accuracy under different conditions of the method described herein, an internal validation study was performed. This consisted of three parts, which tested length measurement on simulated images, length measurement on phantom images, and diameter measurement on phantom images, respectively. During each test, table movement between the acquisition of the two required images was allowed, and used.

EXAMPLE 1

The goal of the first test was to determine a minimum angle between the reference and analysis image to achieve a predefined maximum error of 5%, and to determine the theoretical accuracy of the three-dimensional reconstruction. The method described below was applied to find a particular length in simulated images, and the minimum angle between reference and analysis image to achieve the desired accuracy of 5% was found to be 30°. In fact, at this difference in projection angle, the accuracy is found to be better than 1.5%.

EXAMPLE 2

The goal of the second test was to determine the accuracy of length measurements based upon X-ray images of a phantom vessel. The method described below was applied to find a particular length in phantom images. Phantom images were acquired with an angle difference of at least 30°, and the accuracy of the length measurement was found to be better than 2%.

EXAMPLE 3

The goal of the third test was to determine the accuracy of the diameter measurements based upon X-ray images of a phantom vessel. The absolute accuracy of the diameter was better than −0.1 mm, and the precision was better than 0.2 mm based on phantom images that were acquired with an angle difference of at least 30°. This experiment used contour detection based on the CAAS II quantitative analysis software (Gronenschild, E., J. Janssen, et al. "CAAS. II: A second generation system for off-line and on-line quantitative coronary angiography." Cathet Cardiovasc Diagn 33(1): 61–75 (1994)).

Image Analysis

After the images are captured, an operator in this example embodiment performs an analysis using procedure 200, which will now be discussed with reference to FIG. 2 and continuing reference to objects shown in FIG. 1, beginning at START point 201. The operator first selects (205) a reference image. This image should represent both the part of vessel 160 that is being investigated and at least a part of calibration object 150. The reference image may be captured with or without contrast liquid; in the latter case there is preferably a guide wire or catheter visible in the part of the vessel 160 under investigation.

The reference image is then automatically corrected (step 210) for geometric distortion, as was mentioned above and is understood by those skilled in the art. The operator then indicates (step 215) the midline of the vessel in the reference image by indicating some control points. This step is preferably performed using a graphical user interface to a computer program that displays the reference image, accepts "click" actions by a pointing device to indicate control points, and accepts "drag" actions by a pointing device to move previously indicated control points. When the operator indicates that control point selection is complete, the computer program fits a curve through the indicated points, preferably by using a mathematical parametric curve definition known as splines. Preferably six control points are indicated to define the midline of the vessel.

The operator performs (step 220) a calibration of the pixel size on the sphere in the reference image. This calibration is preferably performed automatically (using edge- and curve-detection techniques known to those in skilled in the art) after the operator indicates a point near the center of the sphere. This calibration method is highly reproducible.

The operator then selects (step 225) a second image, to which this disclosure refers as the analysis image. The analysis image should be acquired using contrast liquid in the part of the vessel 160 that is being investigated and with calibration object 150 visible. The analysis image may be a subtracted image, as will be understood by those skilled in the art. The analysis image is automatically corrected (step 230) for geometric distortion.

The operator then performs (step 235) a calibration on the sphere in the analysis image. Like the calibration in step 220, this is preferably performed automatically after the operator indicates a point near the center of the sphere. If the analysis image is a subtracted image, the calibration should be performed without subtraction.

The computer program then displays (step 240) two lines in the analysis image that indicate the corresponding position of the start and end points of the vascular segment as the operator indicated (step 215) in the reference image.

The operator indicates (step 245) the vascular segment of interest by indicating the start and end points of the approximate centerline. When the operator finishes, the computer program automatically detects the borders of the vessel. This detection is preferably based on the CAAS II contour detection algorithm (see Gronenschild, Janssen, et al., supra). When the contour detection is finished, a number of physical parameters are calculated, such as vessel diameter, vessel segment length, cross sectional area, and the like. To this point these parameters are still based on the two 2-dimensional images only, and are likely to include out-of-plane and/or foreshortening errors. Results will be corrected for these errors in step 260, below.

The midline of the vessel 160 is computed (step 250) based on the borders detected in step 245. A three-dimensional representation of the midline of vessel 160 is then computed (step 255), as will be discussed in conjunction with method 300, below. The geometric results of step 245 are then corrected (step 260) according to the three-dimensional spatial position of the vessel, and method 200 ends at END point 299.

Reconstruction Algorithm

Figure 2:
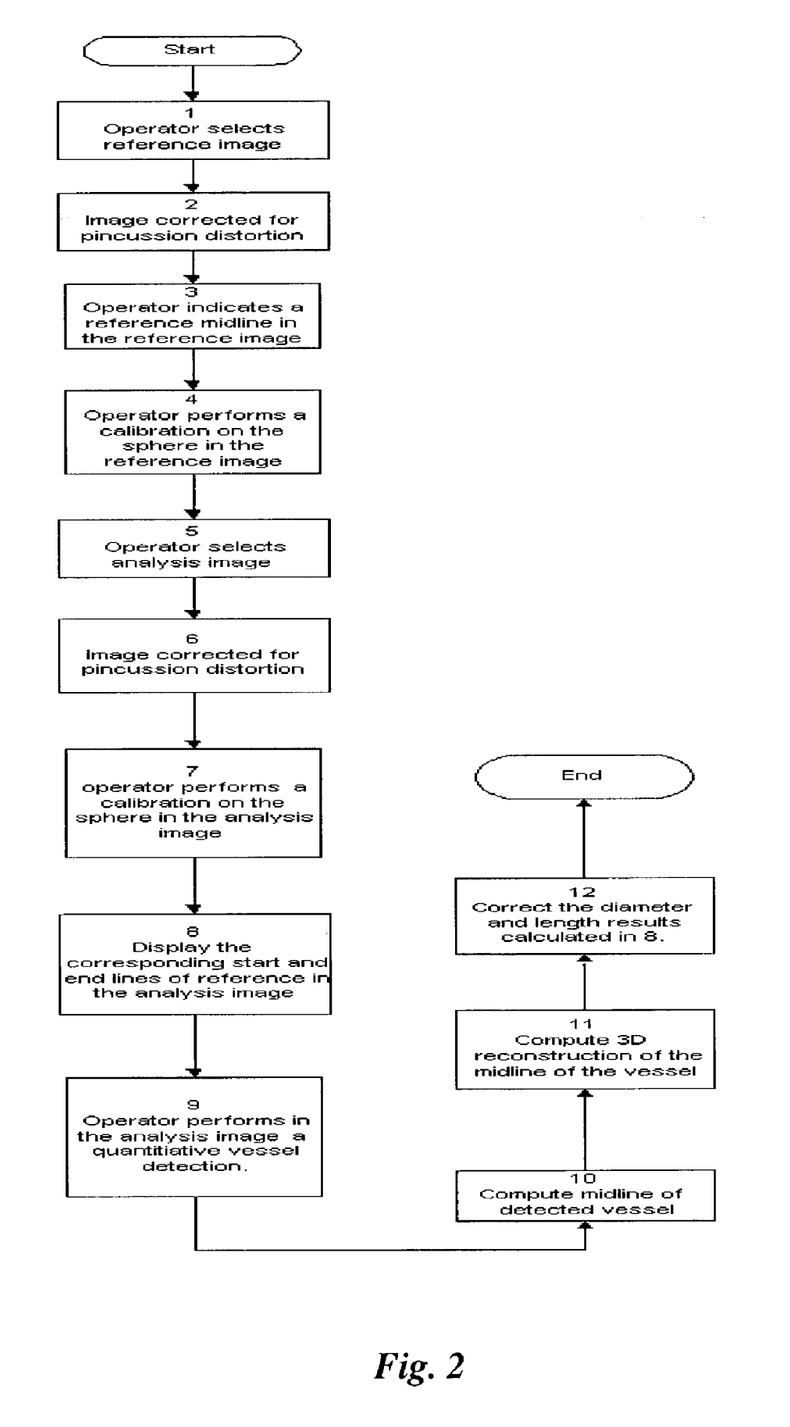
FIG. 2 is a flowchart showing GUI-operator interaction in one method of collecting data for use according to the present invention.
Figure 3:
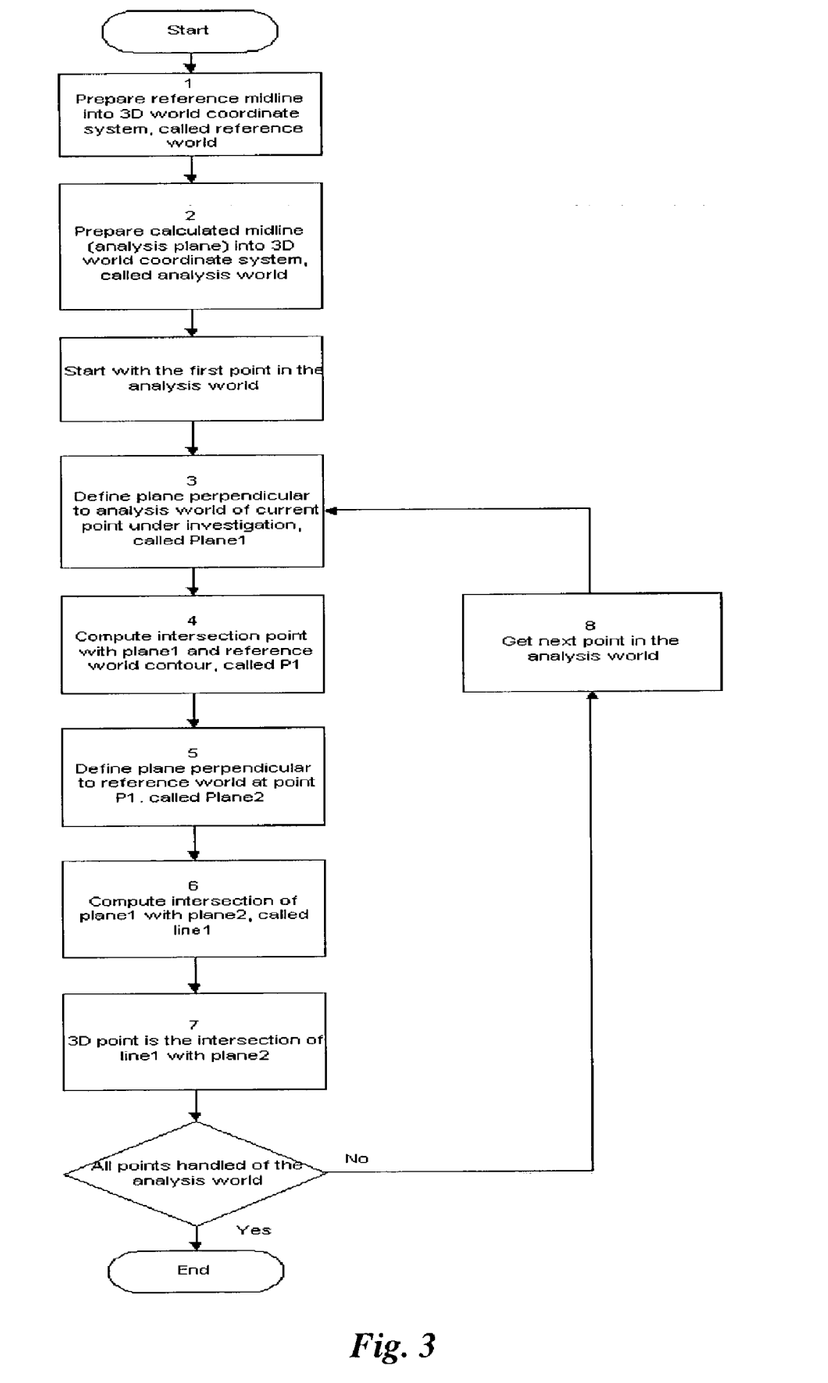
FIG. 3 is a flowchart showing one method of analyzing data according to the present invention.

The three-dimensional reconstruction technique applied in step 255, above, will now be discussed with reference to FIG. 3, and continuing reference to objects and step in FIGS. 1 and 2. The method 300 is based on three assumptions. First, it is assumed that different orientations of the image recording plane are used for the reference and analysis (2-D) images. The angle between the perspective vectors (the normal vectors to the image recording plane as the image is captured) for the two images is preferably between 30° and 150°. Second, at least part of calibration object 150—enough to determine its center and size in the image plane—and the vessel 160 under investigation must be visible in both images. Finally, the distance SID between the X-ray source and the image intensifier, the rotation angle θ, the angulation angle γ, and the pixel size at the image intensifier should be known, as discussed above in connection with the initialization process.

Figure 1:
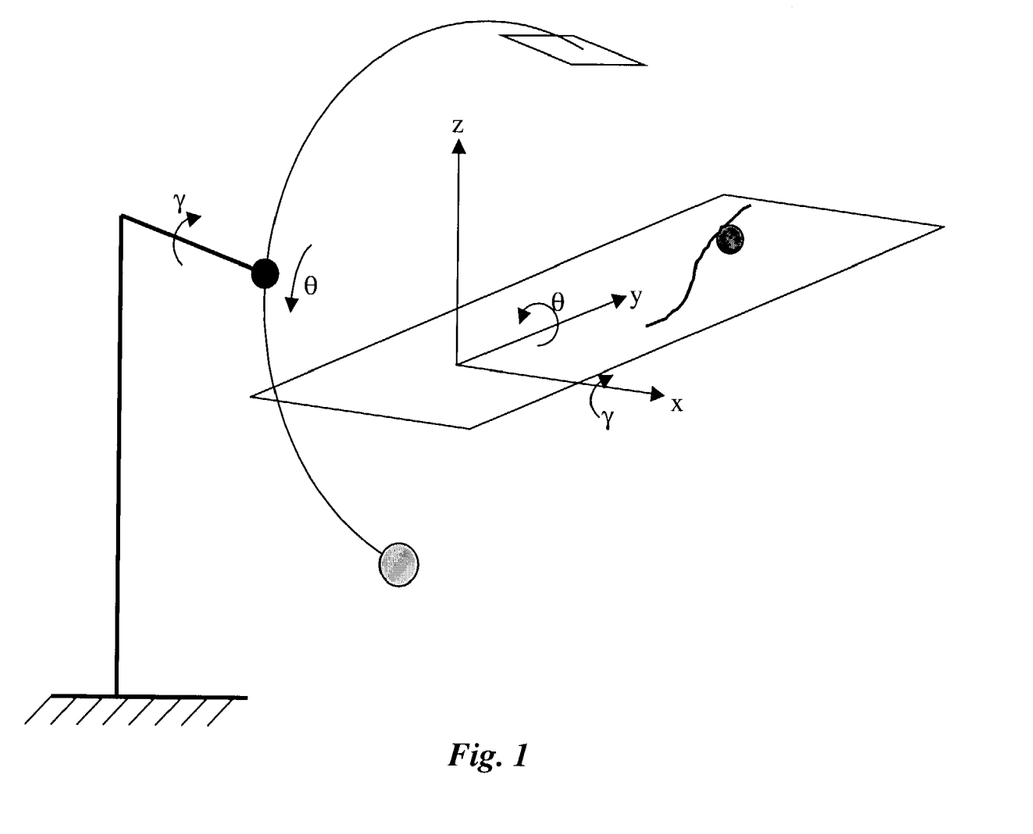
FIG. 1 is a schematic diagram of a testing room having various components of an apparatus for practicing the present invention.

At the beginning of method 300 (START point 301), the two-dimensional midline from the reference image (indicated in step 215) is transformed (step 310) into the coordinate system for the three-dimensional world using a rotation matrix $R(-\gamma, -\theta)$, scaling matrix $S(p_x, p_y)$, and translation matrix $T(-x_{calibration}, -y_{calibration})$. The transformation matrix from reference image to world coordinates is thus:

$$M_{I \rightarrow W\_ref} = R(-\gamma, -\theta) \cdot S(p_x, p_y) \cdot T(-x_{calibration}, -y_{calibration}) \quad \text{[Equation 1]}$$

which converts the two-dimensional coordinates of the reference image into the three-dimensional world coordinate system (see FIG. 1).

Likewise, the two-dimensional midline from the analysis image is then transformed (step 320) into the three-dimensional world coordinate system. This transformation matrix is defined as $$M_{I \rightarrow W\_ana} = R(-\gamma, -\theta) \cdot S(p_x, p_y) \cdot T(-x_{calibration}, -y_{calibration}) \quad \text{[Equation 2]}$$

which converts the two-dimensional coordinates of the analysis image into the three-dimensional world coordinate system.

Figure 4:
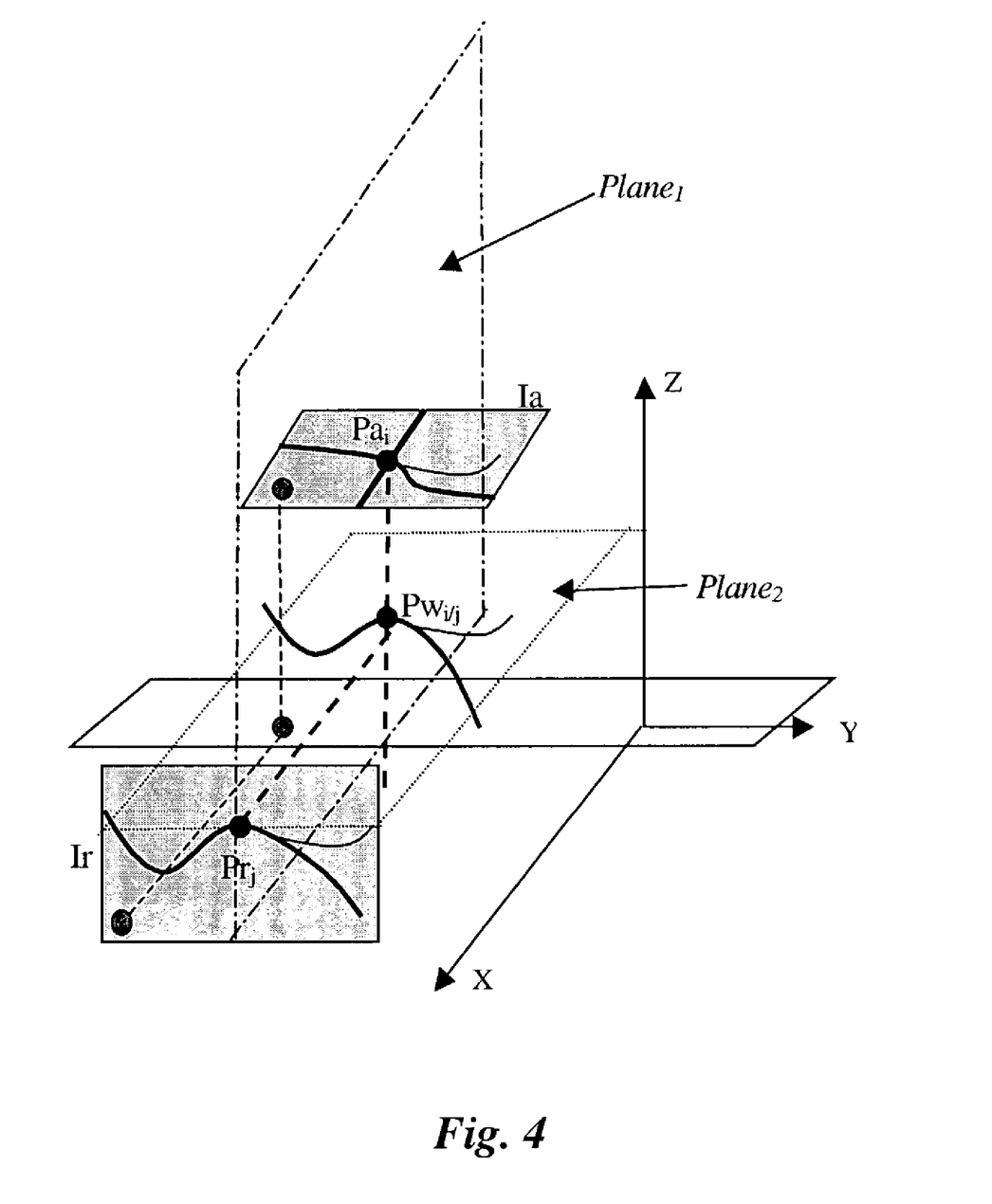
FIG. 4 is a diagram showing spatial features referred to in calculations herein.

For each point in the analysis world contour-wire $W_a$, starting (step 330) with the first point $V_1^{W_a}$, the corresponding point in three-dimensional space will now be determined with reference to the points, lines, and planes illustrated in FIG. 4.

Assume that the contour-wire $W_a$ of the analysis image consists of n elements, and the contour-wire $W_r$ of the reference image consists of m elements. The contour-wires $W_a$ and $W_r$ can now be computed in world coordinates using Equation 1 and Equation 2. For the reference image, the position of each point $V_j^{W_r}$ can be calculated using $$V_j^{W_r} = M_{I \rightarrow W\_ref} \cdot V_j^{I_r}; j = \{1, \ldots, m\} \quad \text{[Equation 3]}$$

and for the analysis image, each point $V_i^{W_a}$ can be calculated using $$V_i^{W_a} = M_{I \rightarrow W\_ana} \cdot V_i^{I_a}; i = \{1, \ldots, n\} \quad \text{[Equation 4]}$$

The real three-dimensional position of the midline wire W is the intersection of the normal vector at $W_a$ with the normal vector at $W_r$ for each segment of wire W.

The plane Plane$_1$ perpendicular to the analysis world is defined (step 340) by $$\text{Plane}_1 = P_{ana_j} + \mu \cdot R_{reference}[2]^T + \lambda \cdot R_{analysed}[2]^T \quad \text{[Equation 5]}$$

$\forall \mu, \lambda \in \Re$. Because the X-ray system can be considered a perspective viewing system, the normal vectors should be corrected. The corrected normal is the normalized vector from X-ray source ($P_1$) to the center of the image intensifier ($P_2$). Thus, $$P_1^{3D} = \begin{pmatrix} 0 \\ 0 \\ -SID \end{pmatrix} \quad \text{[Equation 6]}$$

$$P_2^{3D} = \begin{pmatrix} (P_2^{2D}x - Po_x) \cdot p_{ii} \\ (P_2^{2D}y - Po_y) \cdot p_{ii} \\ 0 \end{pmatrix}$$

$$\vec{n}_{corr} = (R_{ref_r} \cdot R_{ref_a})^{-1} \cdot P_2^{3D} - (R_{ref_r} \cdot R_{ref_a})^{-1} \cdot P_1^{3D}$$

$$\bar{n}_{corr} = \frac{\vec{n}_{corr}}{\|\vec{n}_{corr}\|}$$

The origin of the system can, of course, be shifted out of the origin of the world view, which is the center of calibration object 150. This is done by correction of the position vector of Equation 5. $P_{ana_j}$ should be corrected with the correction (offset) vector. The correction vector is the vector from the center of the image to the center of calibration object 150, rotated over the rotation vector R. That is:

$$V_{corr} = \begin{pmatrix} (P_{sphere2}^{2D}x - Po_x) \cdot p_{sphere} \\ (P_{sphere2}^{2D}y - Po_y) \cdot p_{sphere} \\ 0 \end{pmatrix} \cdot R \quad \text{[Equation 7]}$$

Equation 5 can then be rewritten as:

$$\text{Plane}_1 = V_{corr_1} \cdot P_{ana_j} + \mu \cdot R_{reference}[2]^T + \lambda \cdot R_{analysis}[2]^T \quad \text{[Equation 5.1]}$$

Now find (step 350) the intersection point between Plane$_1$ and the three-dimensional world reference midline:

$$P_{ref_j} = \{(l_{refcontour} \cap \text{Plane}_1^j)\} \quad \text{[Equation 8]}$$

The plane perpendicular to the analysis world is defined (step 360) by:

$$\text{Plane}_2 = V_{corr_2} \cdot P_{ref_j} + \alpha \cdot (R_{reference}[2]^T \otimes R_{analysed}[2]^T) + \beta \cdot R_{reference}[2]^T \quad \text{[Equation 9]}$$

$\forall \alpha, \beta \in \Re$.

Define (step 370) the line l perpendicular to the reference plane at the position found in step 360 for $\forall \alpha \in \Re$:

$$l = P_{ana_j} + \alpha \cdot R_{analysed}[2]^T \quad \text{[Equation 10]}$$

The intersection of Plane$_2$ from step 360 with line l from step 370 is calculated (380) as the three-dimensional coordinate $P_{3D}$:

$$P_{3D} = \{(l \cap \text{Plane}_2^j)\} \quad \text{[Equation 11]}$$

Now that the three-dimensional reconstructed midline of the vessel is available, it is possible to correct the length and diameter for the out-of-plane calibration and foreshortening errors.

If there are more points to handle in the analysis image (decision step 390), the next point in the analysis world contour-wire is retrieved (step 395), and process 300 continues at step 340. When there are no more points (negative result at decision step 390), method 300 ends at END point 399.

The projection of the three-dimensional midline resulting from the three-dimensional reconstruction process is oriented in the world Cartesian coordinate system. Before performing correction based on the three-dimensional midline of the vessel 160 under investigation, it is preferably positioned in the same view as the acquired image. The three-dimensional model, therefore, is preferably rotated to the same orientation as the projection of the analysis image. Spatial parameters of the vessel 160 are then calculated.

The length L of the real-world contour-wire (representing the center line of the vessel 160) can be calculated by summing the lengths of the segments of the three-dimensional midline over the desired segment. For example, when the points on the contour-wire are denoted as $P_k$ for k= 1, . . . m, and the desired segment is from $P_a$ to $P_b$ for some integers a and b, where $1 \leq a < b \leq m$, then the length is:

$$L = \sum_{k=a}^{b-1} \|\overline{P}_k - \overline{P}_{k+1}\| \qquad \text{[Equation 12]}$$

Figure 5:
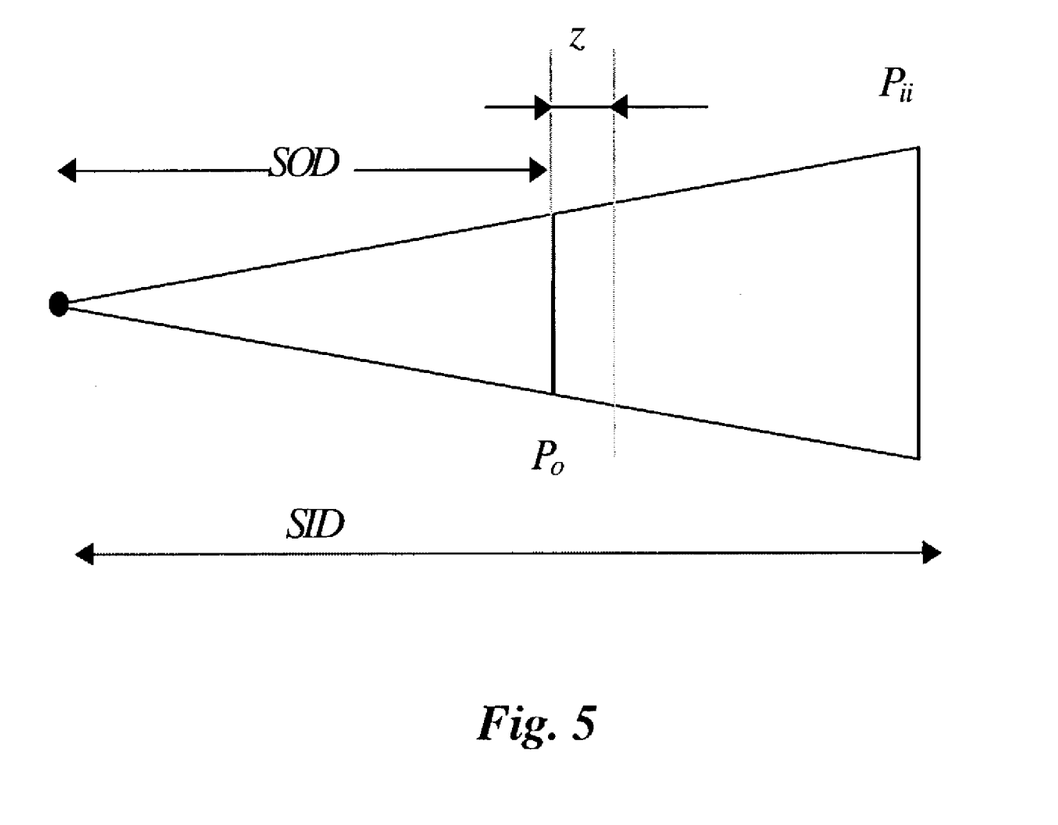
FIG. 5 is a diagram of the relationship among selected distances discussed herein.

In addition, one can calculate a diameter of the vessel 160. After repositioning the three-dimensional midline into the projection of the analysis image, the z-component indicates the out-of-plane distance as shown in FIG. 5. SID represents the source-to-intensifier distance, SOD is the source-to-calibration object distance, $P_o$ is the actual profile of the object, and $P_{ii}$ is the projected profile of the object.

Now the pixel size at each position of the midline is computed. Based on the detected contour we can compute the diameter at each position along the vessel. Summarized, the calculation is:

$$SOD = SID \cdot \left(\frac{p_{calibration}}{p_{ii}}\right) \qquad \text{[Equation 13]}$$

$$SOD_i = SOD + \left\| P_{3D_i} \cdot \begin{vmatrix} 0 \\ 0 \\ 1 \end{vmatrix} \right\|$$

$$p_i = p_{ii} \cdot \frac{SOD_i}{SID}$$

$$D_i = |Edge_{left} - Edge_{right}| \cdot p_i$$

Both length and diameter parameters are then available without out-of-plane or foreshortening errors.

All publications, prior applications, and other documents cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that would occur to one skilled in the relevant art are desired to be protected.

What is claimed is:

1. A method, comprising:
    accessing at least two digital images $I_i$ of a bodily structure and a reference object, where
        each of the digital images shows the bodily structure and at least a portion of the reference object;
        the view direction for each image $I_i$ is defined by a unit vector $v_i$; and
        there are at least two images $I_{i1}$ and $I_{i2}$ taken at different instants, such that there is an angle α between the normal vectors $v_{i1}$ and $V_{i2}$ of the respective images, where $-180° < \alpha < 180°$, and $\alpha \neq 0°$; and
    quantifying one or more spatial parameters of the bodily structure using $I_{i1}$ and $I_{i2}$.

2. The method of claim 1, wherein said one or more spatial parameters is a length.

3. The method of claim 1, wherein said one or more spatial parameters is a diameter.

4. The method of claim 1, wherein said structure is a vessel.

5. The method of claim 1, wherein at least one of images $I_{i1}$ and $I_{i2}$ is a subtracted image.

6. The method of claim 1, wherein a is in the set of angles comprising:
    angles between about −150° and about −30°, and
    angles between about 30° and about 150°.

7. A method, comprising:
    accessing at least two digital images $I_i$ of a bodily structure and a reference object, where
        each of the digital images shows the bodily structure and at least a portion of the reference object;
        the view direction for each image $I_i$ is defined by a unit vector $v_i$; and
        there are at least two images $I_{i1}$ and $I_{i2}$ taken at different instants, such that there is an angle α between the normal vectors $v_{i1}$ and $v_{i2}$ of the respective images, where $-180° < \alpha < 180°$, and $\alpha \neq 0°$; and
    quantifying one or more spatial parameters of the bodily structure using $I_{i1}$ and $I_{i2}$; wherein
    the bodily structure moves between capture of images $I_{i1}$ and $I_{i2}$.

8. The method of claim 7, wherein said one or more spatial parameters is a length.

9. The method of claim 7, wherein said one or more spatial parameters is a diameter.

10. The method of claim 7, wherein said structure is a vessel.

11. The method of claim 7, wherein at least one of images $I_{i1}$ and $I_{i2}$ is a subtracted image.

12. The method of claim 7, wherein a is in the set of angles comprising:
    angles between about −150° and about −30°, and
    angles between about 30° and about 150°.

* * * * *